United States Patent
Rich et al.

(10) Patent No.: US 7,294,839 B2
(45) Date of Patent: Nov. 13, 2007

(54) LOW VOLUME SAMPLE CELL AND GAS MONITORING SYSTEM USING SAME

(75) Inventors: David R Rich, Glastonbury, CT (US); John L Sandor, North Haven, CT (US)

(73) Assignee: RIC Investements, Inc., Wilmington, DE (US)

( * ) Notice: Subject to any disclaimer, the term of this patent is extended or adjusted under 35 U.S.C. 154(b) by 0 days.

(21) Appl. No.: 10/678,683

(22) Filed: Oct. 3, 2003

(65) Prior Publication Data

US 2004/0065835 A1   Apr. 8, 2004

Related U.S. Application Data

(60) Provisional application No. 60/416,875, filed on Oct. 8, 2002.

(51) Int. Cl.
*G01J 5/02*   (2006.01)
*G01N 21/05*   (2006.01)
*G01N 21/35*   (2006.01)

(52) U.S. Cl. ............... 250/343; 250/339.13; 250/437; 73/23.3; 356/440

(58) Field of Classification Search .......... 250/343, 250/339.12–339.13, 437, 338.1, 339.01, 250/339.06, 339.1, 428, 432 R, 435; 73/23.2–23.3; 356/246, 440, 436–437; 600/532, 538; 128/204.22
See application file for complete search history.

(56) References Cited

U.S. PATENT DOCUMENTS

| | | | | |
|---|---|---|---|---|
| 4,681,443 A | * | 7/1987 | Bach et al. | 356/246 |
| 4,823,168 A | * | 4/1989 | Kamahori et al. | 356/246 |
| 5,256,160 A | * | 10/1993 | Clement | 604/319 |
| 5,261,415 A | * | 11/1993 | Dussault | 600/532 |
| 5,282,473 A | | 2/1994 | Braig et al. | |
| 5,616,923 A | * | 4/1997 | Rich et al. | 250/343 |
| 5,657,750 A | | 8/1997 | Colman et al. | |
| 5,693,944 A | * | 12/1997 | Rich | 250/343 |
| 5,789,660 A | * | 8/1998 | Kofoed et al. | 73/23.2 |
| 5,932,877 A | * | 8/1999 | Braig et al. | 250/343 |
| 5,942,755 A | * | 8/1999 | Dreyer | 250/339.13 |
| 6,095,986 A | * | 8/2000 | Braig et al. | 600/532 |
| 6,190,327 B1 | * | 2/2001 | Isaacson et al. | 600/529 |

* cited by examiner

*Primary Examiner*—David Porta
*Assistant Examiner*—Frederick F Rosenberger
(74) *Attorney, Agent, or Firm*—Michael W. Haas (57) ABSTRACT

A sample cell, which is a component of a gas monitoring system, includes a sample cell body and a sample cell core installed therewith. The sample cell is coupled to a sampling tube that communicates with an airway of a patient. Gas from the sampling tube passes through the sample cell such that the flow profile remains substantially undisturbed. Within the sample cell, at least one optical aperture permits radiation to be emitted, pass through the gas in the sample cell core, and detected. In this manner, measurements of the partial pressure or concentration of a gas of interest are determined.

14 Claims, 6 Drawing Sheets

LOW VOLUME SAMPLE CELL AND GAS MONITORING SYSTEM USING SAME

CROSS-REFERENCE TO RELATED APPLICATIONS

This application claims priority under 35 U.S.C. § 119(e) from provisional U.S. patent application Ser. No. 60/416,875 filed Oct. 8, 2002, the contents of which are incorporated herein by reference.

BACKGROUND OF THE INVENTION

1. Field of the Invention

The present invention pertains to a method and apparatus for monitoring gas, and, in particular, to a sample cell for use in such a system and method.

2. Description of the Related Art

It is well-known to those skilled in the art that non-dispersive infrared (NDIR) type gas analyzers operate on the principle that the concentration of specific gases, such as carbon dioxide, nitrous oxide and anesthetic agents, can be determined by (a) directing infrared radiation from an infrared emitter through a sample of a gaseous mixture, (b) filtering this infrared radiation to minimize the energy outside the band absorbed by the specific gases, (c) measuring the radiation impinging upon a infrared radiation detector and which has passed through this sample, and (d) relating a measure of the infrared absorption of the gas to a gas concentration. Gases that may be measured exhibit increased absorption (and reduced transmittance) at specific wavelengths in the infrared spectrum. Moreover, the greater the gas concentration, the greater the absorption and the lower transmittance.

NDIR gas analyzers are widely used in medical applications and can be characterized as either in the main path of the patient's respiratory gases, known as mainstream or non-diverting gas analyzer, or located off of the main path, known as sidestream or diverting gas analyzer. Regardless of whether the analyzer diverts gas or not, the gas to be analyzed must transverse a flow passage in which infrared radiation passes through the gas sample. This portion of the passage, known as a sample cell, confines a sample composed of one or more gases to a particular flow path that is traversed by the optical path between the infrared radiation emitter and the infrared radiation detector. The infrared radiation emitter and an infrared radiation detector are both components of a transducer that may be detachably coupled to the sample cell. Other terminology, such as cuvette or airway adapter, is often used interchangeably with the term sample cell.

Mainstream designs require the optical and/or electronic components to be interfaced to the subject's airway or respiratory circuit. A mainstream analyzer is typically situated such that the patient's inspired and expired respiratory gases pass through the sample cell onto which a transducer, which includes elements necessary for monitoring respiratory gases, may be placed.

On the other hand, in sidestream analyzer designs, the optical and electronic component are typically positioned at a distance away from the subject's airway or respiratory circuit in communication therewith. U.S. Pat. No. 5,282,473, issued to Braig et al., discloses an exemplary sidestream infrared gas analyzer and sample cell. Sidestream gas analyzers typically communicate with a patient's airway by way of a long sampling plastic tube connected to an adapter, e.g., a T-piece at the endotracheal tube or mask connector, positioned along a breathing circuit or a nasal catheter that has been placed in communication with the patient's airway. When positioned along a breathing circuit, the sampling ports used by sidestream sampling systems are typically located in a wall of a component of the breathing circuit. The location of the sampling port along the breathing circuit may range anywhere from an elbow connected to an endotracheal tube to a wye connector at the opposite end of a breathing circuit. Gas passing through the sidestream analyzer is either exhausted to atmosphere or returned to the mainstream respiratory circuit.

As the patient breathes, gases are continuously drawn at sample flow rates ranging from 50 to 250 ml/min from the breathing circuit through the sampling tube and into the sample cell located within or near the monitor. To reduce the time delay associated with the transport of the gas sample through the sampling tube, conventional sidestream systems drawn gas at sample rates of 180 ml/min or higher. However, it is desirable to remove as little gas as possible from the breathing circuit and at the same time faithfully reproduce the gas waveform. Therefore, lower flow rates such as 50 ml/min have been used. In order not to degrade performance, as measured by accuracy of the end-tidal gas values, particularly at higher respiratory rates that may be seen in infants, careful attention must be paid to the total flow path from sampling site to the sample cell. While issues, such as mechanical mixing of the sample during transport in the sample line, and diffusion of the waveform within the sample line during transport, can be addressed by the selection of smaller bore tube, the proper design of the flow path through the sample cell is critical to achieve optimal performance. Present designs of sample cells have sample cell chamber volumes that are too large and/or inlet and outlets that tend to distort the profile of the waveform.

A typical sample cell is molded from an appropriate polymer, and has a passage defining the flow path for the gases being monitored. Typically, the optical path traverses the flow path with optical apertures in the wall of the sample cell and aligned along and on opposite sides of the flow passage. This configuration allows the beam of infrared radiation to enter the sample cell, traverse the gases in the flow passage, and, after being attenuated, exit from the sample cell to the filter and radiation detector. Transmissive windows in the optical apertures confine the gases to the sample cell flow passage and keep out foreign matter, while minimizing the loss of infrared energy as the beam enters and exits from the sample cell. The distance transversed by the infrared radiation in the flow passage of the sample cell is known as the measurement pathlength and is typically the distance between the optical apertures of the sample cell.

At a constant partial pressure or concentration of a gas, as the distance between the optical apertures increases, a greater quantity of the emitted infrared radiation is absorbed at the wavelength(s) specific to the gas of interest due to the presence of a greater number of molecules of the gas of interest. With a ratiometric measurement approach, emitted radiation at another wavelength, where little or no absorption occurs, is concurrently measured, and the ratio of the measurements at the two wavelengths allows the partial pressure of the gas to be determined. Thus, to achieve an acceptably quiet (noise free) and a fast response time for the gas analyzer, both the measurement pathlength and volume of the sample cell must be carefully considered.

Therefore, a need exists for a sample cell that has a low internal volume, minimizes unswept volume, and allows for sufficient pathlength so that an acceptable signal can be measured. Such a design must provide efficient "flushing" of the volume so that the response time is not compromised. Additionally, this needs to be achieved in a manufacturable and commercially viable manner.

SUMMARY OF THE INVENTION

Accordingly, it is an object of the present invention to provide a sample cell that overcomes the shortcomings of conventional sample cells. This object is achieved according to one embodiment of the present invention by providing a sample cell with a low internal volume and that provides a flow path that prevents or minimizes eddies or stagnant areas along the gas flow, so that all gas entering the sample cell is swept out of the sample cell as new gas enters. In particular, the use of a separate sample cell body and sample cell core allows this design to be manufacturable and cost effective. It is to be understood, that that present invention contemplates that the sample cell core can be integrally molded with the sample body so that both elements are formed as a single piece.

More specifically, a sample cell according to the principles of the present invention includes a sample cell body having a first passage defined therethrough. A sample cell core having a second passage defined therethrough is securable to the sample cell body such that the first passage is in fluid communication with the second passage. At least one first optical aperture is defined in the sample cell core to allow light to pass through at least a portion of the second passage. In addition, a first window is disposed over the first optical aperture.

A sample cell according to another embodiment of the present invention includes a sample cell body having a passage defined therethrough, wherein the passage includes: (1) an inlet portion defined along a first axis and adapted to receive a flow of gas, (2) an outlet portion adapted to communicate a flow of gas from the sample cell body, wherein the outlet portion is defined along the first axis such that the inlet portion and the outlet portion are coaxially aligned, and (3) a sample chamber portion disposed between the inlet portion and the outlet portion and in fluid communication with the inlet portion and the outlet portion, and wherein the sample chamber portion is defined along a second axis that is substantially perpendicular to the first axis. A first window is defined in the sample cell body to provide optical access to the sample chamber portion of the passage.

It is a further object of the present invention to provide a gas monitoring system that uses any of the above-described sample cells.

It is yet another object of the present invention to provide a method of sidestream infrared gas measurement that does not suffer from the disadvantages associated with conventional sidestream measurement techniques. This object is achieved by providing a method that includes low sample cell volume, sufficient pathlength and a flow profile that prevents or minimizes eddies or stagnant areas along the gas flow, so that all gas entering the sample cell is swept out of the sample cell as new gas enters. This method of infrared gas measurement comprises drawing a gas through a sample cell that includes the sample cell body and sample cell core. In one embodiment, the sample cell core is secured to the sample cell body such that the passages of each are connected so that the gas may pass smoothly through the sample cell. An infrared radiation source emits a plurality of wavelengths of infrared radiation through an optical aperture in the sample cell core. The wavelengths emitted from the radiation source are sensed by a radiation detector after passing through a volume of the selected gas. The content of the selected gas passed between the radiation source and radiation detector is determined by the amount of infrared radiation from the radiation source that impinges upon the radiation detector.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
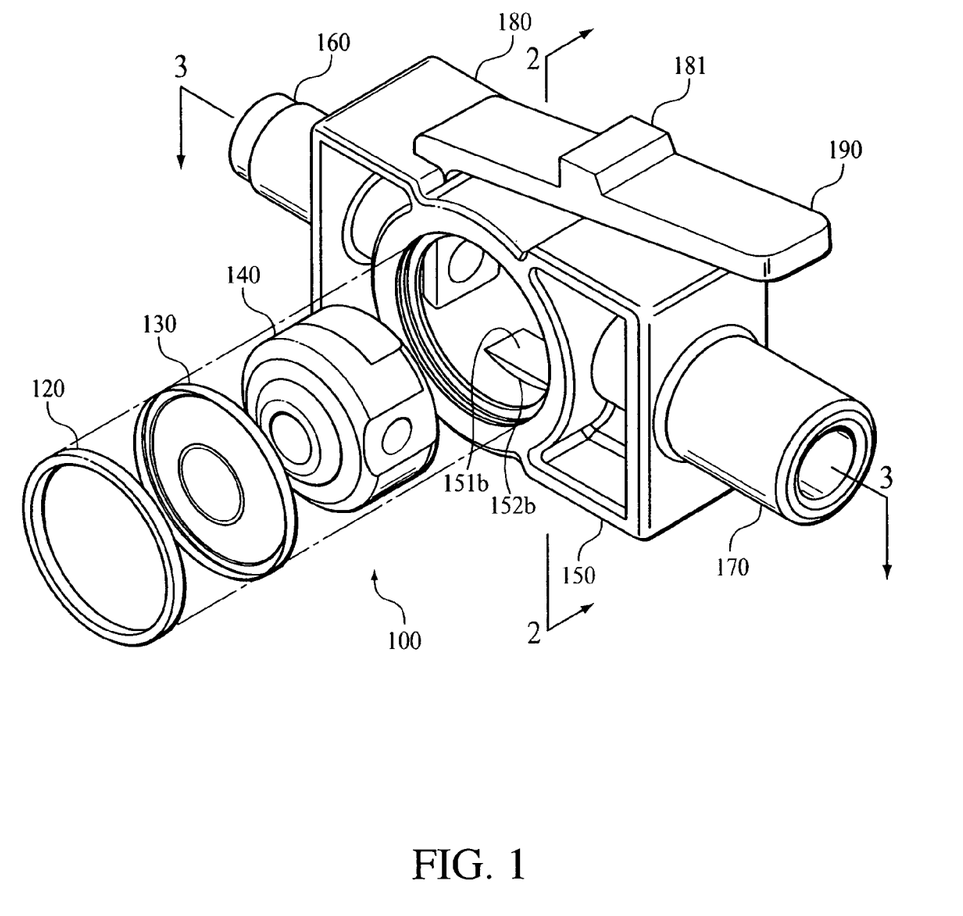
FIG. 1 is an exploded perspective view of the sample cell.

FIG. 1 schematically illustrates an exemplary embodiment of a sample cell 100 according to the principles of the present invention. Sample cell 100 includes a sample cell body 150 and a sample cell core 140. As discussed in greater detail below, sample cell core 140 is removeably attached within sample cell body 150. Gas from a sampling tubing originating in an airway adapter or nasal cannula is drawn through optional filter prior to entering sample cell body 100 via an inlet port 170. Infrared radiation is passed through the gas following through sample cell 100, and a portion of the infrared radiation is absorbed by the gases present in the sample cell. Using an optics configuration coupled to this sample cell, the partial pressure of gases, such as carbon dioxide, can be measured. The gas exits sample cell body 100 via an output port 160 and into a pump prior to exiting via an exhaust or scavenging port.

Figure 8:
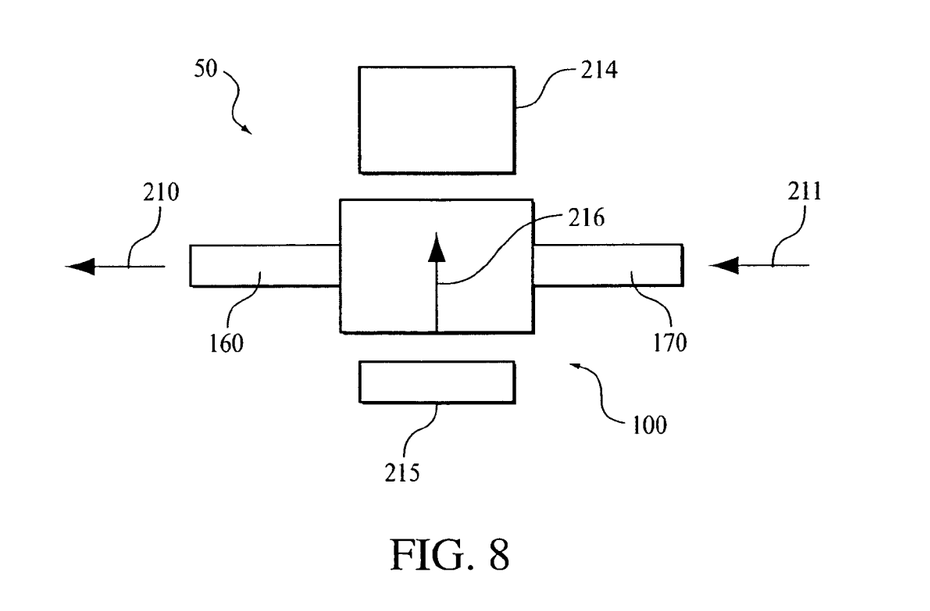
FIG. 8 is a block diagram of a gas monitoring system showing the sample cell, radiation source, and detector.

FIG. 8 depicts a gas monitoring system 50 in block diagram form suitable for use with sample cell 100. As shown in this figure, sample cell 100 is optically and mechanically coupled with a radiation source assembly 215 and a radiation detection assembly 214. The radiation is emitted from radiation source assembly 215, then passes through sample cell 100 (as shown by arrow 216) and enters radiation detection assembly 214. While FIG. 8 illustrates the radiation source and detector as being aligned with one another, it is to be understood, the present invention contemplates that sample cell 100 can be used in a gas monitoring system in which the source and detector are located in other configurations, such as side-by-side, and a reflector, for example, is used to direct the radiation back to the detector.

Referring again to FIG. 1, sample cell 100, or sample cell body 150, may be positioned either temporarily or permanently within the measurement optics, which include a radiation source assembly and radiation detector assembly. The infrared radiation from source assembly passes through a window 130 of sample cell body 150 into the interior of sample cell core 140, where a portion of the radiation is absorbed by the gas in the sample cell core. The transmitted radiation then may either pass through another window (not shown) or reflect and pass again through window 130. Window 130 is secured to sample cell body 150 via a snap-in retainer ring 120. In either case, a detector assembly eventually converts the transmitted radiation into signals that are sampled and converted into a measured value.

The sample cell described may be located within the monitor, detachable and as a separate module. The optics may be configured so that the sample cell can be secured and detached easily by the user via a latching mechanism. The sample cell would be removable with a positive latch and may provide identification to the monitor as to the sampling set type, as well as any calibration information via optical or mechanical schemes. Latch 190 attaches to upper surface of sample cell 100 via a latch base 180. Tab 181 of latch 190 allows the aforementioned positive latching and permits sample cell to be removably secured to a gas monitoring system.

Figure 2:
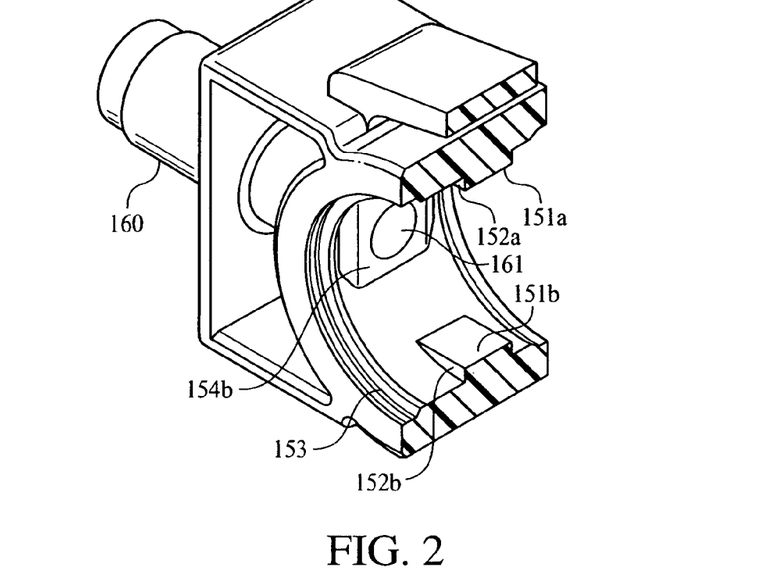
FIG. 2 is a cross-sectional perspective view of the sample cell body taken substantially along line 2-2 of FIG. 1.

To facilitate ease of construction and provide for transitions between the passages within sample cell core 150 and sample cell body 100, the sample cell core is mechanically keyed to insure radial alignment of these flow passages. FIG. 2 depicts sample cell body alignment shelves 151*a* and 151*b* and sample cell body alignment stops 152*a* and 152*b* to which the corresponding sample cell core alignment shelves and stops mate. Sample cell core 140 is press fit into sample cell body 150, and is properly aligned via the sample cell body alignment shelves and stops. Flat protrusion 154*b* mates with the flat outer surface 146*b* of sample cell core 140 as to form a leak-free junction between passage 141 of sample cell core 140 and passage 161 of sample cell body 150, as well as the corresponding passages 142 of the sample cell core and passage 171 of the sample cell body shown in FIG. 6.

Snap-in retaining rings 120 immobilize the windows in a parallel, spaced apart relationship with a selected, accurately reproducible optical path length between the snap-in retainer rings. The perimeter of snap-in retainer ring 120 seats in a snap ring undercut 153 within the perimeter of the optical aperture. Snap-in retaining rings are installed such that the windows are held flat and distortion free.

Figure 3:
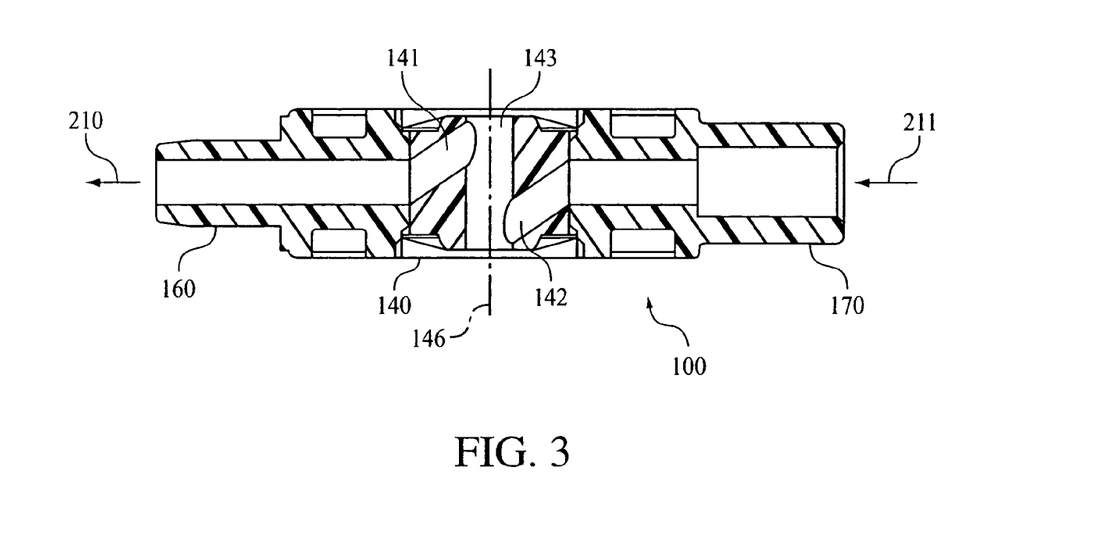
FIG. 3 is a cross-sectional view taken substantially along line 3-3 of FIG. 1.

FIG. 3, a cross-sectional view of the exemplary embodiment in FIG. 1 taken substantially along line 3-3, depicts the flow of gas through passages within sample cell body 150 and sample cell core 140. The gas enters the sample cell (arrow 211) after passing through the sampling tubing and an optional means to remove fluids before entering the sample cell such as a filter. After the gas passes through a passage within inlet port 170, it enters the passage located within the sample cell core 140. Within sample cell core 140, the gas enters a sample chamber 143 adjacent to the window at one end and exits adjacent to the window at the opposite end. The sample cell chamber is the portion of the passage through which radiation passes. Sample chamber 143 of the preferred embodiment is of a cylindrical design with the inlet and outlet positioned at opposite ends, as close to the windows as possible permit the sample gas to cleanly pass without crevices, eddies, and other "unswept" volumes (sometimes referred to as "deadspace") where gas can remain stagnant. Due solely for compatibility with prior optical configurations, the measurement pathlength was predefined at 0.300" and a nominal aperture of 0.100" was chosen. After passing out of sample cell core 140, the gas exits sample cell 100 after passing through the passage within outlet 160 (arrow 210). The sample cell core preferably located in the central portion of the sample cell both provides a passage for the gas sample between the symmetrical inlet and outlet passages in the body.

The optical path of sample cell 100 of the present invention does not simply transverse the flow path, but rather is parallel with the flow path for a substantial portion of the path length. To achieve this alternative flow path and minimize the disturbance to the flow profile, a flow passage shape, referred to as the "Z" configuration, is used in this embodiment of the present invention. The use of the "Z" configuration of the flow passage allows for optimal flushing of the volume of sample cell 100 by directing the flow of the gas sample intimately adjacent to the sample cell windows. This configuration also allows for the uniform flow passage from outside the sample cell, into the sample cell body and sample cell core without unnecessary transitions and the resultant turbulence. This "Z" configuration effectively eliminates small volumes of "unswept" gas at the windows that tend to reduce response time and add an uncontrollable and variable error component.

However, this configuration is challenging to manufacture since it is not possible to injection mold such a configuration in one piece. This problem is overcome by separating a portion of the sample cell into a separately moldable part, the sample cell core. These parts referred to as sample cell core and sample cell body allow both the desired performance goals and ease of manufacture to be achieved. While this may also be achieved with a sample cell of greater than two part and, therefore, greater complexity, a two part solution is preferred. Note that alternatives to the "Z" configuration may also be used, provided that adequate pathlength is maintained and the flow profile is not sufficiently disturbed.

Figure 4A:
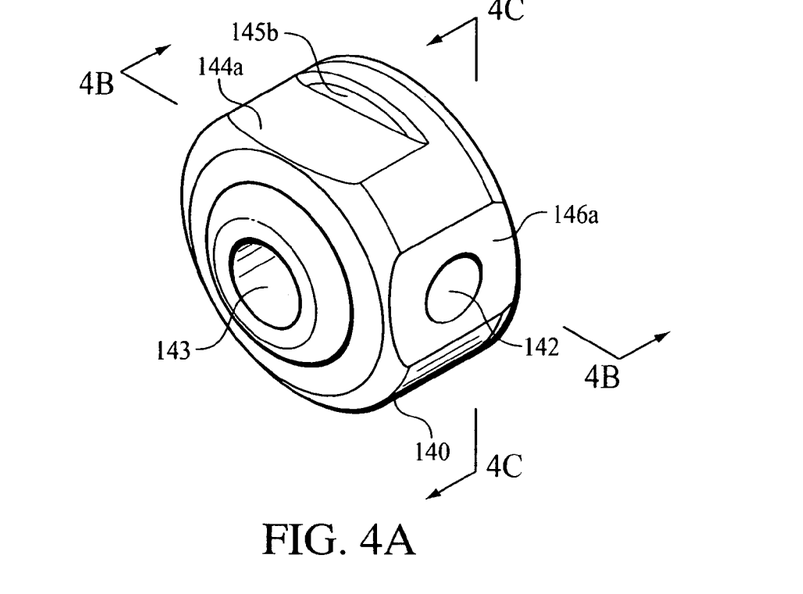
FIG. 4A is perspective view of the sample cell core.
Figure 4B:
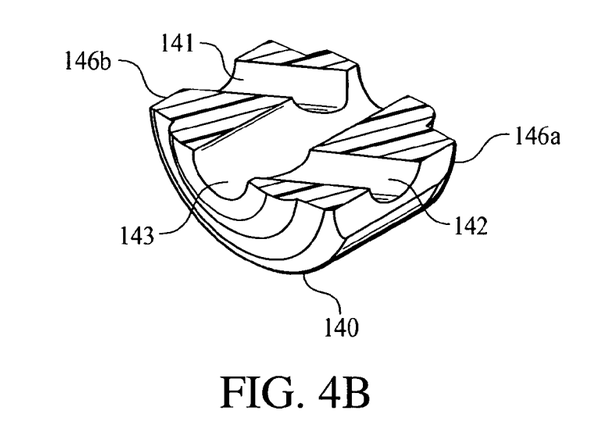
FIG. 4B is the cross-sectional perspective view taken substantially along line 4B-4B of FIG. 4A.
Figure 4C:
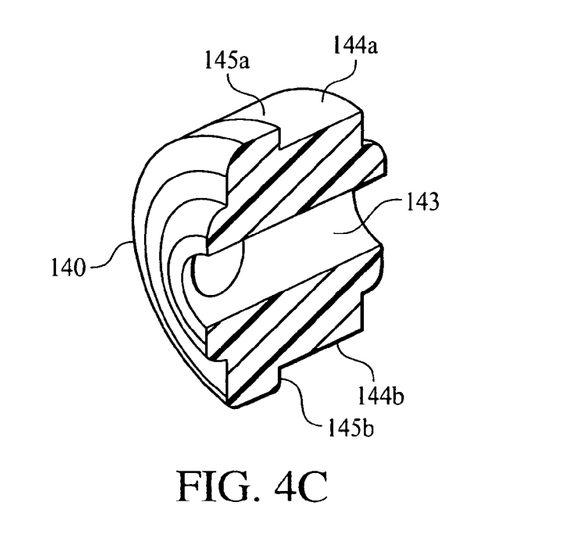
FIG. 4C is a cross-sectional perspective view taken substantially along line 4C-4C of FIG. 4A.

FIG. 4A depicts a perspective view of sample cell core 140 of the exemplary embodiment in FIG. 1. FIG. 4B depicts a cross-sectional view of sample cell core 140 in FIG. 4A. Sample cell core shelves 144*a* and 144*b* are designed such that when situated with the corresponding sample body alignment shelves and sample body alignment stops in the sample cell body, the exterior ends of a passage 142 and a passage 141 are aligned with the corresponding passages within the sample cell body forming an effectively smooth and leak free transition so that the flow profile is not disturbed and no gas escapes from the connection formed. Sample cell core alignment stops 145*a* and 145*b* are placed so that sample cell core when press fitted into the sample cell body, placed to the desired depth on the sample cell body and no further.

Figure 5:
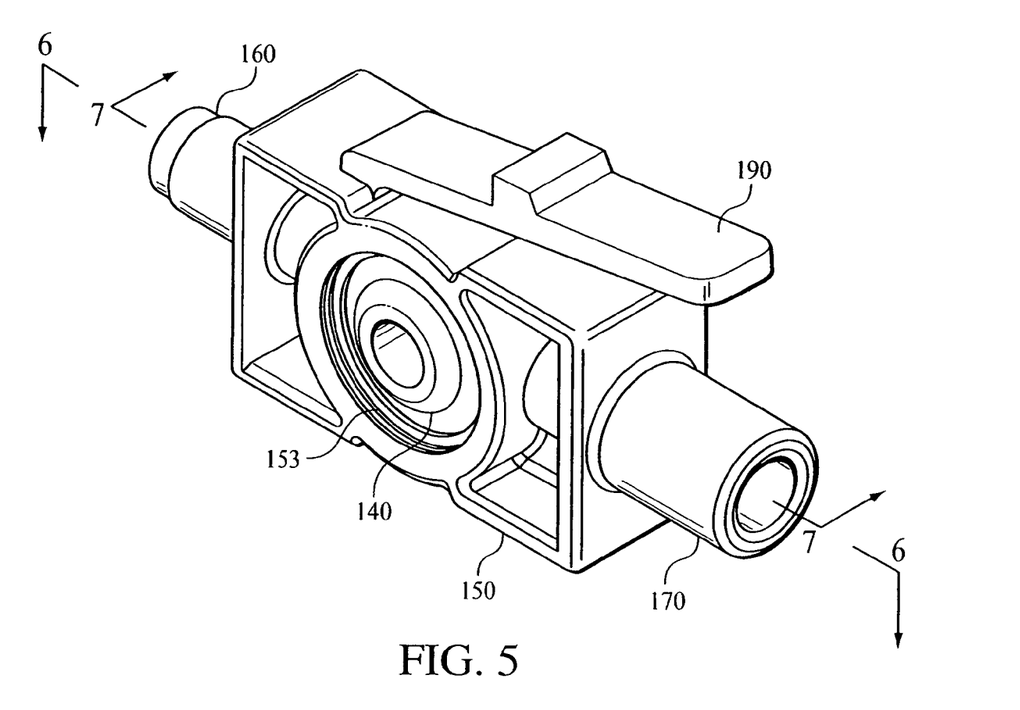
FIG. 5 is a perspective view of the sample cell body with the sample cell core inserted.

FIG. 5 depicts sample cell 100 with sample cell core 140 installed, but without window 130 and snap-in retainer ring 120. In this perspective view, snap ring undercut 153, located within the perimeter of the optical aperture and adjacent to the installed the sample cell core, is clearly shown.

Figure 6:
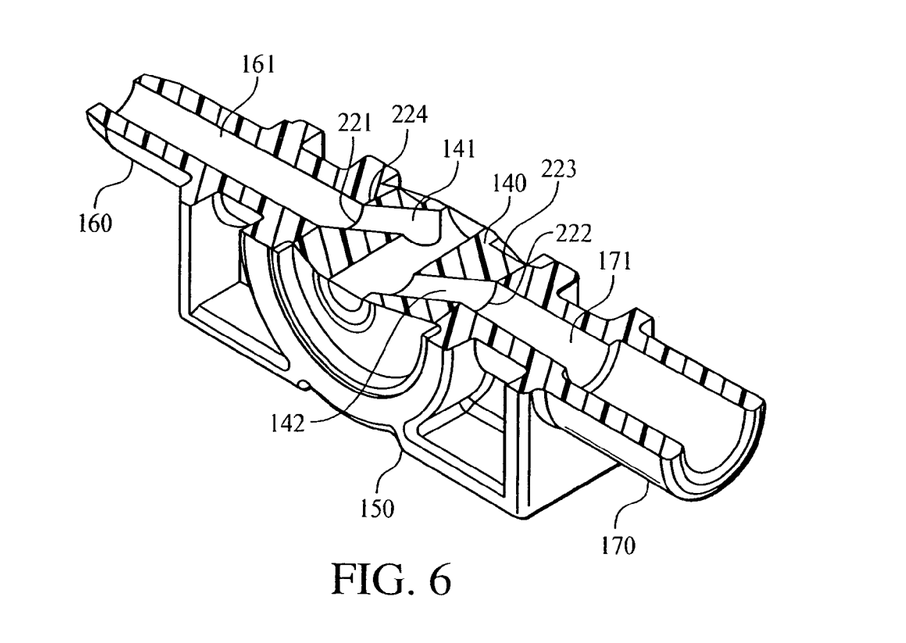
FIG. 6 is a cross-sectional perspective view of the sample cell core taken substantially along line 6-6 of FIG. 5.

FIG. 6, a cross-section of the perspective view of the sample cell in FIG. 5, depicts the criticality of the proper alignment of the passages of sample cell core 140 and sample cell body 150 at junctions 221 and 222. Flat outer surfaces 146a and 146b of the sample cell core and flat protrusions 154a and 154b of the sample cell body form a seal around the junction of these passages at junctions 223 and 224. The alignment shelves and stops depicted in FIG. 1 and 2 allow these surfaces to properly align when sample cell core 140 is press fit into sample cell body 150.

Figure 7:
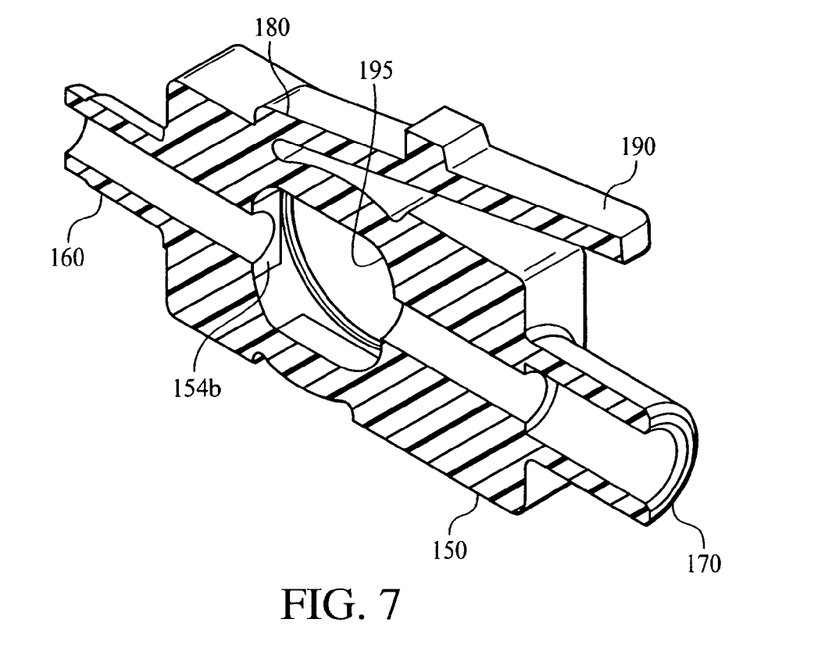
FIG. 7 is a cross-sectional perspective view of the sample cell body, without the sample cell core, taken substantially along line 7-7 of FIG. 5.

FIG. 7 is a cross-section of the perspective view of sample cell 100 taken along line 7-7 in FIG. 5. It should be noted that FIG. 7 depicts sample cell 100 without the sample cell core. In use, the sample cell core is located in a chamber 195.

Figure 9:
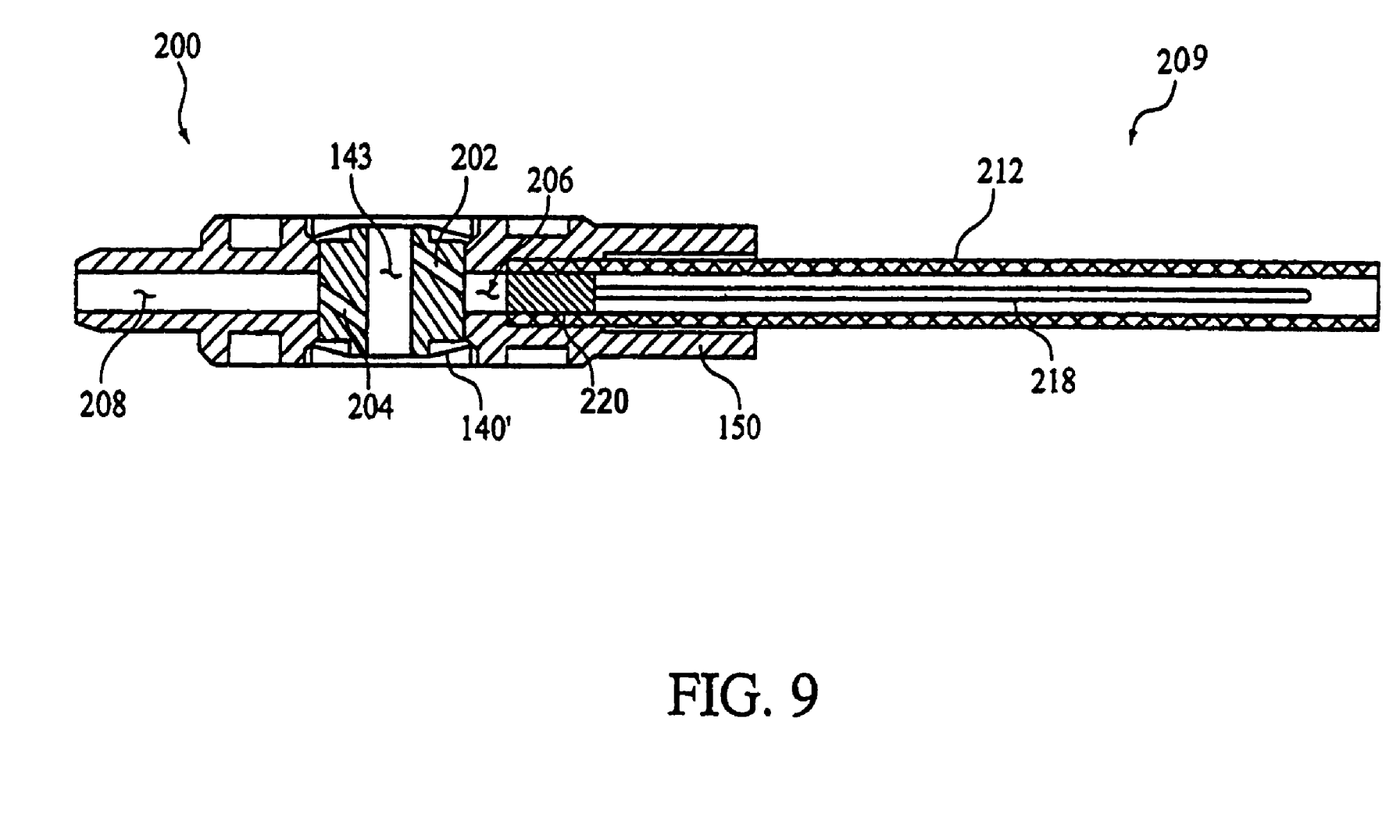
FIG. 9 is cross-sectional perspective view of the sample cell according to a further embodiment of the invention.

FIG. 9 is a cross-sectional view of another embodiment of a sample cell 200 according to the principles of the present invention. Sample cell 200 is, in most respects, the same as sample cell 100 in the previous embodiment and, FIG. 9 illustrates a view of the sample cell taken along the same section lines as that of FIG. 3. Sample cell 200, like the sample cell of the previous embodiments, includes a passage defined through a sample cell body 150 and a sample cell core 140'. However, in this embodiment, a diameter for passages 202 and 204, which couple an inlet portion 206 and an outlet portion 208 to sample cell chamber 143, are less than that shown, for example, in FIG. 3. This embodiment emphasizes that the diameters for the portions of the passage through the sample cell can be varied, so long as the functions of the present invention, such as minimizing unswept volume, are achieved.

FIG. 9 also illustrates a filter assembly 209 coupled to sample cell 200. Filter assembly 209 includes a filter tubing 212 in which are provided at least one filter element 218 coupled to a mounting block 220. As is known in the art, filter elements are hydrophobic in that they allow gas to pass through them, while preventing liquids from passing. It is to be understood that the present invention contemplates using the sample cell of the present invention in combination with any type of filter. However, in a preferred embodiment, the filter structure used with the sample cell is that disclosed in co-pending U.S. patent application Ser. No. 60/416,874, the contents of which are incorporated herein by reference.

While the above-embodiments describe the sample cell body and the sample cell core as being formed from two separate pieces that are joined together. It is to be understood that the present invention contemplates that these items can be defined from a common structure. That is, sample cell body and the sample cell can be a single piece. In addition, the present invention contemplates that the features of the sample cell body and the sample cell core can be provided using other structures. For example, a two-piece assembly can be provided, where each piece provides elements of both the sample cell body and the sample cell core so that when joined the sample cell of the present invention is formed.

This invention relates to the design of a sample cell for use in a sidestream gas sampling system. In particular, the present invention relates to a sample cell configuration that facilitates analysis without loss of signal fidelity (degradation of the input waveforms) at low sample flow rates.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A sidestream sample cell comprising:

a sample cell body having a cell body width, a cell body length, a longitudinal axis defined along the length of the sample cell body, a first port defined in a first end of the sample cell body, a second port defined in a second end of the sample cell body, and a first passage defined in the sample cell body generally between the first port and the second port, wherein the first port and the second port are coaxially aligned with the longitudinal axis of the sample cell body;

a sample cell core having a cell core width, a cell core length, and a second passage defined in the sample cell core such that the second passage has a generally "Z-shaped" configuration through the sample cell core, wherein a central leg of the second passage is defined through the sample cell core in a direction corresponding to the cell core width and generally perpendicular to the longitudinal axis of the sample cell body, wherein the first passage is in fluid communication with the second passage, and wherein the sample cell core includes at least one first optical aperture defined therein to allow light to pass through the central leg of the second passage; and a first window disposed over the first optical aperture, and wherein the cell core width in combination with a thickness of the first window is not less than the cell body width so that the cell core width in combination with the thickness of the first window defines a maximum width of the sample cell over a length of the sample cell body that inserts into a sidestream gas monitoring system.

2. The sample cell of claim 1, wherein the sample cell core further includes at least one second optical aperture defined therein, and wherein the second optical aperture is optically aligned with first optical aperture; and further comprising:

a second window dispose over the second optical aperture.

3. The sample cell of claim 1, wherein in addition to the central leg, the second passage includes a first leg coupling the first port to a first end of the central leg, and a second leg coupling the second port to a second end of the central leg.

4. The sample cell of claim 3, wherein a portion of the "Z-shaped" configuration is adjacent to the first window.

5. The sample cell of claim 1, further comprising at least one snap-in retainer ring positioned around the first window.

6. The sample cell of claim 1, wherein the sample cell core is selectively attachable to the sample cell body, and wherein the first passage defined in the sample cell body includes a chamber adapted to receive the sample cell core.

7. The sample cell of claim 6, wherein the sample cell core is mechanically keyed to insure alignment of the first and second passages during assembly of the sample cell core to the sample cell body.

8. A sidestream gas monitoring system comprising:

(a) a sidestream gas monitor comprising:

(1) a radiation source adapted to emit a plurality of wavelengths of infrared radiation absorbable by a selected gas, and (2) a radiation detector positioned to sense radiation of a plurality of wavelengths emitted from the radiation source, whereby the amount of infrared radiation from the radiation source that impinges upon the radiation detector is proportional to the content of the selected gas passed between the radiation source and radiation detector, and wherein the radiation source and the radiation detector are spaced a first distance apart; and (b) a sample cell having at least one passage defined therethrough, and wherein the sample cell includes at least one first optical aperture defined therein to allow the plurality of wavelengths of infrared radiation from the radiation source to pass through at least a portion of the passage, wherein the sample cell includes:

(1) a sample cell body having a cell body width, a cell body length, a longitudinal axis defined along the length of the sample cell body, a first port defined in a first end of the sample cell body, a second port defined in a second end of the sample cell body, and a first passage defined in the sample cell body generally between the first port and the second port, wherein the first port and the second port are coaxially aligned with the longitudinal axis of the sample cell body, (2) a sample cell core having a cell core width, a cell core length, and a second passage defined in the sample cell core such that the second passage has a generally "Z-shaped" configuration through the sample cell core, wherein a central leg of the second passage is defined through the sample cell core in a direction corresponding to the cell core width and generally perpendicular to the longitudinal axis of the sample cell body, and wherein the first passage is in fluid communication with the second passage, and (3) a first window disposed over the first optical aperture, and wherein the cell core width in combination with a thickness of the first window is substantially the same as the first distance and is not less than the cell body width, so that the cell core width in combination with the thickness of the first window defines a maximum width of the sample cell over a length of the sample cell body that inserts into the sidestream gas monitor.

9. The gas monitoring system of claim 8, wherein the sample cell core is selectively attachable to the sample cell body, wherein the first passage defined in the sample cell body includes a chamber adapted to receive the sample cell core, and wherein the sample cell core is mechanically retained within the chamber.

10. The gas monitoring system of claim 8, wherein the sample cell core is mechanically keyed to insure alignment of the first passage and the second passage.

11. The gas monitoring system of claim 8, wherein in addition to the central leg, the second passage includes a first leg coupling the first port to a first end of the central leg, and a second leg coupling the second port to a second end of the central leg.

12. The gas monitoring system of claim 11, wherein a portion of the "Z-shaped" configuration is adjacent to the first window.

13. The gas monitoring system of claim 8, further comprising:
at least one second optical aperture defined in the sample cell, wherein the second optical aperture is optically aligned with first optical aperture; and
a second window disposed over the second optical aperture.

14. The gas monitoring system of claim 8, further comprising: at least one snap-in retainer ring positioned around the first window.

* * * * *